United States Patent
Mill et al.

(10) Patent No.: US 11,787,314 B2
(45) Date of Patent: Oct. 17, 2023

(54) COMMERCIAL VEHICLE AND RAIL SYSTEM PASSENGER SEAT FOR PASSENGER COMFORT, SAFETY, AND CONVENIENCE

(71) Applicants: Juergen Mill, Ellwangen (DE); Emin Sezgin, Bursa (TR)

(72) Inventors: Juergen Mill, Ellwangen (DE); Emin Sezgin, Bursa (TR)

( * ) Notice: Subject to any disclaimer, the term of this patent is extended or adjusted under 35 U.S.C. 154(b) by 358 days.

(21) Appl. No.: 16/873,467

(22) Filed: Apr. 17, 2020

(65) Prior Publication Data
US 2021/0323449 A1    Oct. 21, 2021

(51) Int. Cl.
*B60N 2/24* (2006.01)
*B60N 2/00* (2006.01)
(Continued)

(52) U.S. Cl.
CPC ............... *B60N 2/242* (2013.01); *A61F 7/08* (2013.01); *A61F 7/10* (2013.01); *A61H 9/0078* (2013.01); *B60N 2/002* (2013.01); *B60N 2/5657* (2013.01); *B60N 2/5685* (2013.01); *B60N 2/5692* (2013.01); *B60N 2/66* (2013.01); *B60N 2/976* (2018.02); *B60R 11/02* (2013.01); *B60R 16/03* (2013.01); *B60R 16/037* (2013.01); *B60R 22/48* (2013.01); *B61D 33/0007* (2013.01); *B61L 3/006* (2013.01); *G05B 19/4155* (2013.01); *G06K 19/06037* (2013.01); *G06Q 10/02* (2013.01); *G06Q 20/045* (2013.01);
(Continued)

(58) Field of Classification Search
None
See application file for complete search history.

(56) References Cited

U.S. PATENT DOCUMENTS

| 7,334,839 B1 | 2/2008 | Malerba |
| 2008/0042483 A1 | 2/2008 | Humer et al. |
(Continued)

FOREIGN PATENT DOCUMENTS

KR    2007 0112339 A    11/2007

OTHER PUBLICATIONS

Turkish Office Action in Priority Case, dated Nov. 24, 2022.
Machine Translation of Turkish Office Action noted above.
Machine Translation of Bibliographic Data for KR20070112339(A).

*Primary Examiner* — James J Lee
*Assistant Examiner* — Tawri M McAndrews
(74) *Attorney, Agent, or Firm* — Ryan M. Fountain

(57) ABSTRACT

A passenger seat for commercial vehicles and rail systems, having at least: a massage pad for increasing the ergonomics in the waist section of the passenger and applying massage; a compressor for inflating the massage pad; cooling pads for cooling the passenger; a heating pad for heating the upper portion of the seat and the backrest contacting the passenger; a presence sensor for determining whether there is a passenger on the passenger seat; a belt sensor for determining whether the passenger fastens the safety belt; a wireless charging unit for the passenger to charge a mobile device without using a connection cable; a manual control panel for the heating pad, cooling pad and the massage pad; a wireless connection module for the heating pad, cooling pad and the massage pad; and a control unit where the data collected from the presence sensor and belt sensor are transmitted.

16 Claims, 4 Drawing Sheets

(51) Int. Cl.
*B60N 2/56* (2006.01)
*B60R 16/03* (2006.01)
*B60R 11/02* (2006.01)
*B60N 2/66* (2006.01)
*B60R 16/037* (2006.01)
*B60R 22/48* (2006.01)
*B61L 3/00* (2006.01)
*B61D 33/00* (2006.01)
*G06Q 50/30* (2012.01)
*G06K 19/06* (2006.01)
*G06Q 10/02* (2012.01)
*G06Q 20/04* (2012.01)
*G05B 19/4155* (2006.01)
*A61H 9/00* (2006.01)
*A61F 7/08* (2006.01)
*A61F 7/10* (2006.01)
*B60N 2/90* (2018.01)
*A61F 7/00* (2006.01)
*B60R 11/00* (2006.01)
*B60Q 3/76* (2017.01)

(52) U.S. Cl.
CPC ...... *G06Q 50/30* (2013.01); *A61F 2007/0024* (2013.01); *A61F 2007/0057* (2013.01); *A61H 2201/0149* (2013.01); *A61H 2201/1238* (2013.01); *A61H 2201/1409* (2013.01); *A61H 2205/081* (2013.01); *B60Q 3/76* (2017.02); *B60R 2011/0012* (2013.01); *B60R 2022/4816* (2013.01); *G05B 2219/50333* (2013.01); *G06Q 2240/00* (2013.01)

(56) References Cited

U.S. PATENT DOCUMENTS

| | | | |
|---|---|---|---|
| 2008/0296939 A1* | 12/2008 | Bajic | B60N 2/5642 297/180.1 |
| 2016/0304013 A1* | 10/2016 | Wolas | B60N 2/5657 |
| 2016/0354027 A1* | 12/2016 | Benson | A61B 5/1102 |
| 2017/0283086 A1* | 10/2017 | Garing | B64D 45/0051 |
| 2018/0333293 A1 | 11/2018 | Lem et al. | |

\* cited by examiner

COMMERCIAL VEHICLE AND RAIL SYSTEM PASSENGER SEAT FOR PASSENGER COMFORT, SAFETY, AND CONVENIENCE

TECHNICAL FIELD

The present invention is related to a new passenger seat which is developed for the commercial vehicles and rail systems that are used in the passenger transport. Furthermore, the present invention is related to a system for using data obtained from a passenger seat in a commercial vehicle or a rail system in passenger traffic.

The invention is particularly related to a passenger seat which comprises a seat sensor, belt sensor, wireless charging system together with heating, cooling, massage functions, in which all features are controlled by a panel integrated on the armrest or a control panel with mobile application, in which the passenger can perform operations such as calling the hostess, giving order, displaying map etc. which will increase the comfort of journey as well as enables adjusting all functions on a single panel.

STATE OF THE ART

Today vehicles used in the highway and rail systems such as busses, minibuses and the like are used in the urban and intercity passenger transportation. It is important that the vehicles used in particularly intercity passenger transportation shall fulfil the comfort requirements of the passenger since the journey duration is long. The human engineering of the seats in the vehicle where the passengers sit is the most important factor in providing comfort.

Many studies were performed in order to make the bus seats more comfortable and bus seats which have many features such as the backrest of the seat back, sled movement of the seat, multimedia screens added to the seat backrest portion, and movable head are developed. On the other hand, in order to provide comfort of the passengers, the number of seats in the bus and their positions has been changed over time. Particularly passenger seats which are single and double have been used in order to increase the knee distance and enlarge the seating surface of the seat. The user requirements have been changed together with the developing technology although changing usage positions of the seats provided an advantage.

Besides, the passenger can be able to adjust his/her seat according to the seating position in the direction of the choices of the passenger. The air temperature to which he/she is exposed during the journey has a great effect on comfort. Particularly, in vehicles with large internal volume, it is not possible to keep the temperature equal in the front and rear section of the vehicle. Although the passengers who sit in the front of the vehicle are exposed to ventilation intensively, this air does not reach the passenger who sits in the rear part. This condition leads to high ambient temperature in the rear part. Particularly when the air temperature in the rear part is required to be reduced, opening the air conditioner may cause the passengers in the front part to feel cold. In order to eliminate this problem, seats which have its own ventilation system namely which can be able to make heating and cooling, are developed. This technology widely used in the passenger cars is integrated in the public transportation because of the change in the passenger requirements.

Another important matter in terms of the passenger transportation is to control whether all passengers who bought tickets are present in the vehicle before the journey starts. Today this control is performed by a person in charge just before the bus takes out. The person in charge wanders in the bus and compares the passenger list and the seats one by one and approves whether all passengers are in their place or not. After performing this control, the person in charge gets out of the vehicle and the bus takes out when no passenger is absent. In order to perform this control properly, it shall be performed just before the bust departure time. In case it is performed earlier, the counting cannot be performed properly since there will be passengers who have not seat their places yet. Late departure of the bus may take place based on the fact that the control is performed at the time of departure and it takes time to count all passengers by the person in charge. One the studies performed for the automatic detection of the passengers who sit in their seats is the invention subject to the patent application No TR 2011/09047 titled as "Mechanism detecting the passenger who sits on bus seats". The invention is a system which transmits an information to the central computer on the bus regarding to which seat is used between which kilometres when the passenger sits on the bus seat, saves this information and also transmits this information to another computer outside the bus by means of GPS navigation system.

In this context, another problem is that drivers of these vehicles sometimes allow passengers to board without issuing them a regular ticket. The drivers then do not give the money they take from the passengers to the vehicle operator, but keep it for themselves.

Another important matter regarding the intercity passenger transportation is that all passengers fasten their seat belts during the journey. Most of the passengers do not fasten their seat belts although seat belt ensures safety during their journey. Today, there is no system in the buses which displays whether the belt is fastened or not and gives a warning when the belt is not fastened. In order to allow for all passengers to fasten their belts, a person in charge is required to wander within the vehicle and to warn passengers who do not fasten their belts one by one. This method is not applicable in practice.

One of the studies performed for improving the seats used in the intercity passenger transportation and for increasing the passenger comfort by adding new features is the invention subject to the utility model No TR 2019/13774 titled as "Functional Development in Passenger Seats". The invention is related to the development of a passenger seat which can be used in all vehicles that transport passengers on land, sea and airways, is multi-functional by means of adding 5 functional features. The inventive seat is characterized by comprising USB and AUX input/output which is not influenced by the vibration of the road. Although the connection is not influenced from the vibration of the road, it is not sufficient to fulfil the comfort conditions required by the passenger.

Another study is the invention subject to the utility model No TR 2018/05684 titled as "Inspection Registration and Warning System controlling the Safety of the Passengers in the Land, Sea and Air Vehicles". The invention is an electronic control system which provides real time registration of the passenger who gets out of the vehicle at the station and stops in order to transport the passenger to the destination in a safe manner. It comprises; control display/monitor including the passenger settlement plan and multi-language supported voice driver warning system, cabin audible warning system connected to the cabin music/announcement system, for the passengers; belt lock sensor, seat weight sensor, internal temperature probe, for the cabin;

camera supported image processing unit, door, window, cover security sensor, temperature, air quality, fire sensor, barcode or wireless label sensor etc. control probes. The connection is made to the control panel in which the system sensor is one or more. All control panels are connected to the control panel by means of a single cable. The control unit has wireless communication units which can be able to realized various safety scenarios, provide visual and audible warning and messages with a plurality of/required language, perform the required controls by means of the programmable inputs and outputs, enable real time recording and reporting. The invention is related to establishing a communication network in the vehicle consisting of control panel and sensors and to an audible warning to the passengers with the driver control responsible of the control system in a plurality of languages in order to transport the passengers on the seats of the land, airway and sea vehicles, to report their safety conditions, to follow them online. The system is an inspection recording and warning system which instantly controls the safety of the passengers in the seats of the land, sea, airway vehicles, characterized in that, it consists of; control unit comprising passenger and/or load placing plan, monitor, flexible sensor network cables, control panel where all cables are combined for flexible sensor network cable branching, sear sensor cable, passenger seat, seat weight (fullness) sensor, door, window, cover condition sensor, automatic door, safety belt lock sensor, safety belt, driver information/main control unit display, main control unit function keys, main control unit keypad, main control unit settlement template, a figure showing the seat condition as full, a figure showing the seat condition as empty, remote control of central control unit.

As a result, the requirement for a new passenger seat which eliminates the abovementioned problems and the insufficiency of the current solutions makes it necessary to make a development in the relevant technical field.

BRIEF DESCRIPTION OF THE INVENTION

The present invention is related to a new passenger seat which fulfils the abovementioned requirements, eliminates all disadvantages and brings some additional advantages, is developed to be used in the commercial vehicles and rail systems that are used in the passenger transport.

The aim of the invention on the basis of the state of the art is to allow all passengers to adjust their own seats according to their preferences both from the panel on the seat and through mobile devices easily and to fulfil comfort requirements completely during the journey, since the developed passenger seat comprises heating, cooling, massage functions as well as seat sensor, belt sensor, wireless charging system, wireless connection and control panel.

The aim of the invention is to increase the ergonomics of the waist region of the passenger by the massage pad located on the backrest of the passenger seat and to apply massage to the waist region.

The aim of the invention is to give sense of cooling to the passenger by the cooling pads located in the seat portion and the backrest portion of the passenger seat.

Another aim of the invention is to fulfil the warming-up requirement of the passenger by means of the fabric with electrical resistance positioned in the seat and backrest portion of the passenger seat in case the ambient temperature is not sufficient.

Another aim of the invention is to determine automatically whether there is a passenger on the seat or not by means of the presence sensor positioned on the bottom portion of the seat portion of the passenger seat, thus to eliminate the requirement of counting the passengers one by one by a person in charge and the time loss in the step of counting process.

Another aim of the invention is to control instantly and separately whether the safety belt of each passenger is fastened or not by means of the belt sensor positioned in the safety belt buckle of the passenger seat.

Another aim of the invention is to allow the passengers to charge their mobile devices easily without using connection cable by means of the wireless charging unit attached to the passenger seat.

Another aim of the invention is to provide the user to charge his/her mobile device by means of a connecting cable via a USB inlet positioned on the passenger seat.

Another aim of the invention is to allow each passenger to make the adjustment of the seat on the basis of comfort requirements by controlling all functions of the seat portion where the passenger sits, by means of a manual control panel integrated on the armrest of the passenger seat.

Another aim of the invention is to enable the passengers to make their seat adjustments through their mobile phones by means of the wireless connection module of the passenger seat.

Another aim of the invention is to allow the passengers to manage comfort settings of the passenger seat, to call hostess, to give an order, to display information such as advertisement, map, regional promotion, weather and road conditions by means of connecting to his/her seat through the mobile application of the passenger via the QR code located on the passenger seat.

Another aim of the invention is to allow the assistant to check e-ticket, to display whether each passenger sits in the correct purchased passenger seat and to manage massage, heating, cooling, presence sensor, belt sensor by means of the main control panel where the data received from the main control unit is included within the passenger seat.

Another aim of the invention is to allow managing the features of the seats in the vehicle by means of a main control unit included in the passenger seat.

Another aim of the invention is to allow mounting all electrical components, sensor circuits, electronic cards, cooling motors, heating resistors and massage compressor motors on the seat by means of the energy panel attached to the passenger seat.

Another aim of the invention is to fulfil the requirement of the passenger without disturbing other passengers in case the passenger desires to read anything or needs light by means of the reading lamp attached to the handle part of the passenger seat.

Furthermore, according to claim 17 a system for using data obtained from a passenger seat in a commercial vehicle or a rail system in passenger traffic is provided.

The system for using data according to the present invention enables digital, i.e. computer-aided or programmed processing and profitable exploitation of information on the condition of the passenger and the passenger seat that the passenger has booked online or at another point of sale.

In this respect, the main control unit may be is operatively connected to a monitoring device of an operator of the vehicle, so that data can be transmitted from the main control unit to the monitoring device of the operator. This enables the operator of the vehicle, for example a bus company, to monitor the occupancy of the vehicle, so that it can be ensured that a driver of the vehicle only allows access to the vehicle to those passengers who have previously purchased a ticket directly from the operator. In other words, the illegal sale of tickets by the driver is thus prevented.

The structural and characteristic features of the present invention will be understood clearly by the following detailed description and therefore the evaluation shall be made by taking the detailed description into consideration.

Another aim of the invention is to manage the whole system by means of the software program which is developed specifically for the invention.

BRIEF DESCRIPTION OF DRAWINGS

In order to understand the advantages of the present invention with its structure and additional elements, it shall be evaluated with the following defined figures.

REFERENCE NUMBERS

Figure 1:
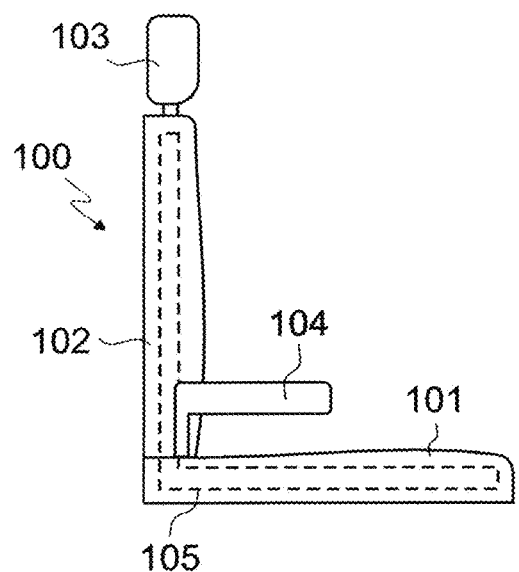
FIG. 1 is a schematic view of a passenger seat according to the invention.

1 Compressor
2 Air pipe
3 Massage pad
4 Snail fan
5 Air channel
6 Cooling pad
7 Heating pad
8 Presence sensor
9 Presence sensor receiver
10 Belt sensor
11 Seat energy panel
100 Passenger seat
101 Seat portion
102 backrest
103 headrest
104 armrest
105 main frame
200 vehicle
201 main control unit

DETAILED DESCRIPTION OF THE INVENTION

In this detailed description, the inventive new passenger seat 100 developed for use in commercial vehicles and rail systems used in the passenger transportation is described only for clarifying the subject matter illustratively and in a manner such that no limiting effect is created.

The inventive passenger seat 100 mainly comprises the following; a seat or seat portion 101 on which the passenger sits and which is mounted parallel to the vehicle floor; a backrest or backrest portion 102 which is engaged with said seat portion 101 and on which the passenger lies back; a headrest 103 which is engaged to the upper portion of said backrest 102 and on which the passenger rests his/her head; an armrest 104 which is engaged on at least one side of the passenger seat 100, preferably is engaged to the point of junction of the seat portion 101 and the backrest 102, can be opened and closed for allowing the passenger to rest his/her arm; a safety belt buckle K which is engaged to the point of junction of the seat 101 and the backrest 102, to which the safety belt (not shown) is fastened.

Figure 2:
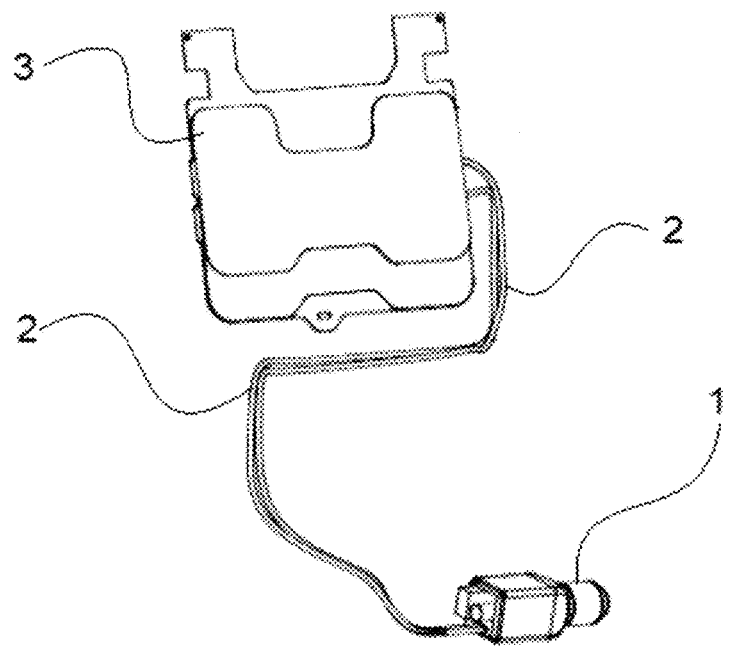
FIG. 2 is a schematic general view of the disassembled condition of the massage pad, air pipes and compressor.

A massage pad 3 is positioned within the backrest 102 of said passenger seat 100, is under the upper covering and engaged to a main structure or main frame 105. The massage pad 3 which is shown is FIG. 2 is engaged with a compressor 1 positioned in the lower section of the seat facing the floor by means of the air pipes 2. The air delivered to the air pipes 2 by said compressor 1 fills in the massage pad 3 and inflates the massage pad 3. The volume of said massage pad 3 is increased when it is inflated in the backrest portion 102 and it leads to the outward protrusion of the upper portion covered with fabric where the passenger rests his/her back. The backrest inflated together with said massage pad 3 allows increasing the ergonomics at the waist part of the passenger and provides a massage effect to the waist part. First of all, it is required to press the button for massage functions through the mobile device connection or through the button located on the manual control panel by the passenger in order to use the massage feature of the inventive passenger seat 100. When the button is pressed, the air within the compressor 1 in the energy control panel is transferred to the massage pads 3 by means of the air pipes 2 and when the massage pads 3 are inflated, the massage function performs its function.

Figure 3:
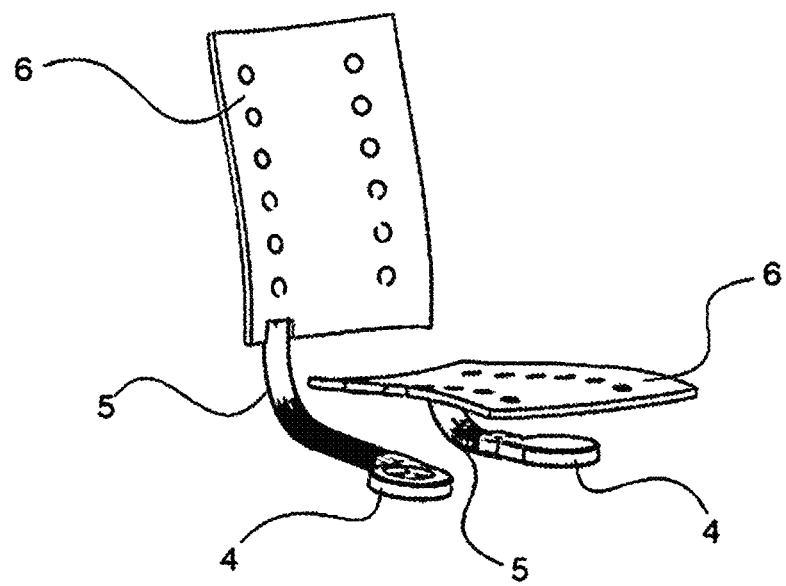
FIG. 3 is a schematic general view of the disassembled condition of the fan, air channel and cooling pad.

Cooling pads 6 are located between the frame 105 on the massage pad 3 positioned in the backrest portion 102 of said passenger seat 100 and within the seat portion 101 and the fabric covering the upper portion. The number of the cooling pads 6 shown is FIG. 3 is two, namely one of them is in the backrest 102 and the other one is in the seat 101. The cooling pad 6 located in said seat portion 101 is engaged to the framework 105. Said cooling pads 6 are connected to a fan 4, in the present case a snail fan, which is located on the bottom surface of the seat facing the floor by means of the air channel 5. The air supplied by said snail fan 4 into the air channels 5 reaches to the cooling pads 6 and then it is supplied to the surface on which the passenger sits by means of the cooling pads 6 for cooling the passenger. First of all, it is required to press the cooling function button located on the mobile device or the manual control panel with 3 levels (low/medium/high) in order to use the cooling feature of the inventive passenger seat 100. The snail fans 4 which are located in the energy control panel generate air and supply the to the air channels 5 when the button is pressed. Said air channels 5 provide air flow in the cooling pads 6 of the seat 101 and the backrest 102 and provide the cooling function to be performed.

Figure 4:
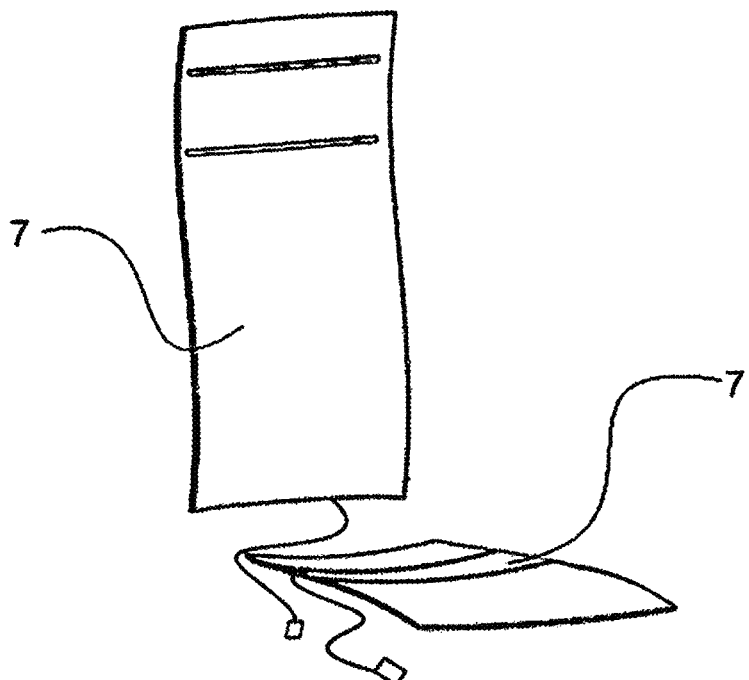
FIG. 4 is a schematic general view of the disassembled condition of the heating pad.

A heating pad 7 is located between the cooling pads 6 and the top cover fabric within the backrest portion 102 and seat portion 101 of said passenger seat 100. The heating pads 7 which are shown in FIG. 4 are made of a fabric with electrical resistance. Energy required for the operation of said heating pads 7 is provided by means of a power unit integrated to the passenger seat 100 or the vehicle main body. In case the passenger requires warming up, the heating pads 7 are activated and the upper portion of the backrest 102 contacting the passenger is heated and its temperature is increased. First of all, it is required to press the heating function button located on the mobile device or the manual control panel with three levels (low/medium/high) in order to use the heating feature of the inventive passenger seat 100. The electrical system in the energy control panel reaches to the resistance in the heating pads 7 of the seat 101 and backrest 102 when the button is pressed and the pads 7 are heated and the heating function is realized.

Figure 5:
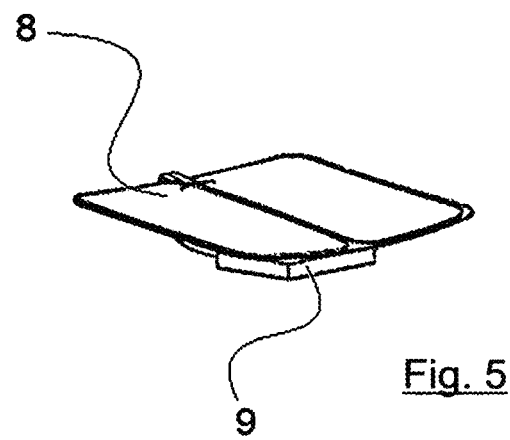
FIG. 5 is a schematic general view of the disassembled condition of the presence sensor and presence sensor receiver.

A presence sensor or occupancy sensor 8 is positioned between the seat main frame 105 and cooling pad 6 in said seat portion 101 of the passenger seat 100. A presence sensor receiver 9 which is engaged with the presence sensor 8 shown in FIG. 5 transmits the information of whether there is a passenger on the passenger seat 100 detected by the presence sensor 8 to a main control unit 201 contained in the vehicle 200 which is shown schematically in FIG. 8. The assistant can be able to obtain the number of the passengers by means of said presence sensor 8 without wandering within the vehicle 200 and controlling the passenger seats 100 one by one.

Figure 6:
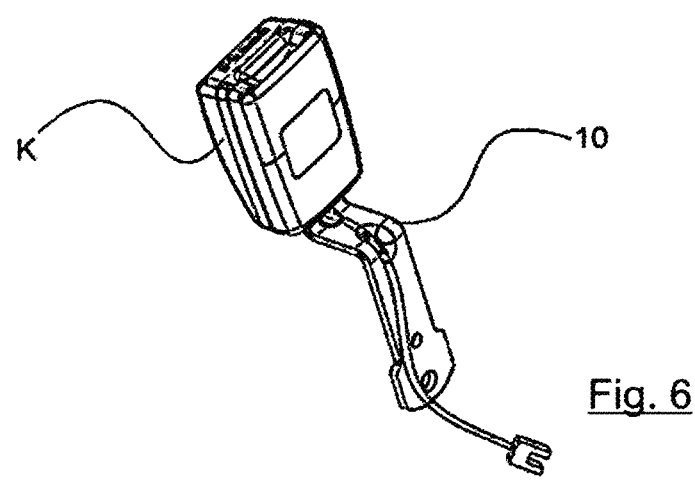
FIG. 6 is a schematic view of the disassembled condition of the safety belt buckle and belt sensor.

A belt sensor 10 is integrated to the belt buckle K which is located at the point of junction of the backrest 102 and seat 101 portions, on side portion of said passenger seat 100. The belt sensor 10 shown in FIG. 6 detects whether the safety belt is fastened to the safety belt buckle K or not. It can be controlled whether the passengers fasten their seat belts or not by means of said belt sensor 10.

A wireless charging unit is located on the upper rear section of the backrest 102 of said passenger seat 100. Said wireless charging unit allows the passenger sitting on the seat to charge his/her mobile device in fast and practical manner without using connection cable. There is a handle made of an elastic material which is located on the upper rear section of the backrest portion 102 of the passenger seat 100 in order to keep the mobile device stable during charging process.

The manual control panel mentioned above is located on said armrest 104 it may, however, be located in another place on the passenger seat 100 where it is accessible to the passenger. Said manual control panel allows the passenger to control the heating pad 7, cooling pad 6 and massage pad 3 and thus the heating, cooling and massage features. The passenger activates or deactivates the required features by means of said manual control panel. There is a wireless connection module in order to allow the passenger to control the heating pad 7, cooling pad 6 and massage pad 3 and thus the heating, cooling and massage features through the mobile device. The passenger enables the connection between the passenger seat 100 and the mobile device of the passenger by using a wireless connection module which is engaged on the seat preferably on the lower portion, Bluetooth and/or Wi-Fi technology. The passenger can be able to control all functions of the passenger seat 100 through his/her own mobile device by means of a mobile application downloaded to the mobile device of the passenger. First of all, the passenger downloads the mobile application to his/her device in order to control the feature settings of the passenger seat 100 from his/her mobile device. Then the identification label on the passenger seat 100 is read by the application and the connection between the passenger seat 100 and the device is established. Said identification label is QR code. After the passenger seat 100 is introduced to the application running on the mobile device, the heating, cooling and massage features can be controlled through the mobile device or the passenger. On the other hand, the passenger can call the hostess, give an order, access regional news and maps, rent a car, hotel or room and display the weather-road condition by means of using the mobile application. The passenger can be able to check and fulfil all requirements over the mobile device during journey by means of the mobile application.

Said passenger seat 100 is managed by means of a main control unit 201 positioned within the vehicle 200. Data which are collected by said presence sensor 8 and belt sensor 10 are transmitted to the control unit. Data transmitted to the aforementioned main control unit 201 is displayed and managed by means of a main control panel. The assistant performs the ticket control through the main control panel, in order to detect whether each passenger sits on the correct seat number corresponding to the ticket which is preferably purchased by means of a mobile device and whether there are absent passengers in the vehicle or not. In case the passenger calls the hostess or gives an order, the assistant can be able to respond through the main control panel by displaying the demand.

A USB input/output is positioned on the handle engaged to the rear portion of the backrest 102 or the headrest 103 in order to allow the passengers who sit on said passenger seats 100 to establish a wired connection for charging the mobile device in case it is required. Energy to said USB input/output is provided by means of a power unit integrated to the passenger seat 100 or the vehicle body.

Figure 7:
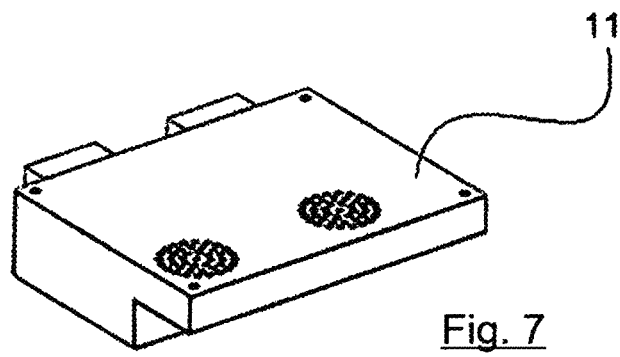
FIG. 7 is a schematic view of the disassembled condition of the seat energy panel.

All electrical components, sensor circuits, electronic cards, cooling motors, heating resistors and top portion of the compressor 1 engine which are engaged to the lower portion of the seat portion 101 of said passenger seat 100 are closed by means of a seat energy panel 11. The power unit shown in FIG. 7 can be positioned within the seat energy panel 11 and also can be engaged to the seat portion 101 of the passenger seat 100 or to the vehicle body separate from the seat energy panel 11 based on the design of the vehicle.

A reading lamp is also engaged to aforementioned passenger seat 100 which the passenger can be able to use in case extra light is needed. The reading lamp engaged on the handle positioned on the rear part of the head portion of said passenger seat 100 fulfils the requirement of light of the passenger without disturbing other passengers.

Figure 8:
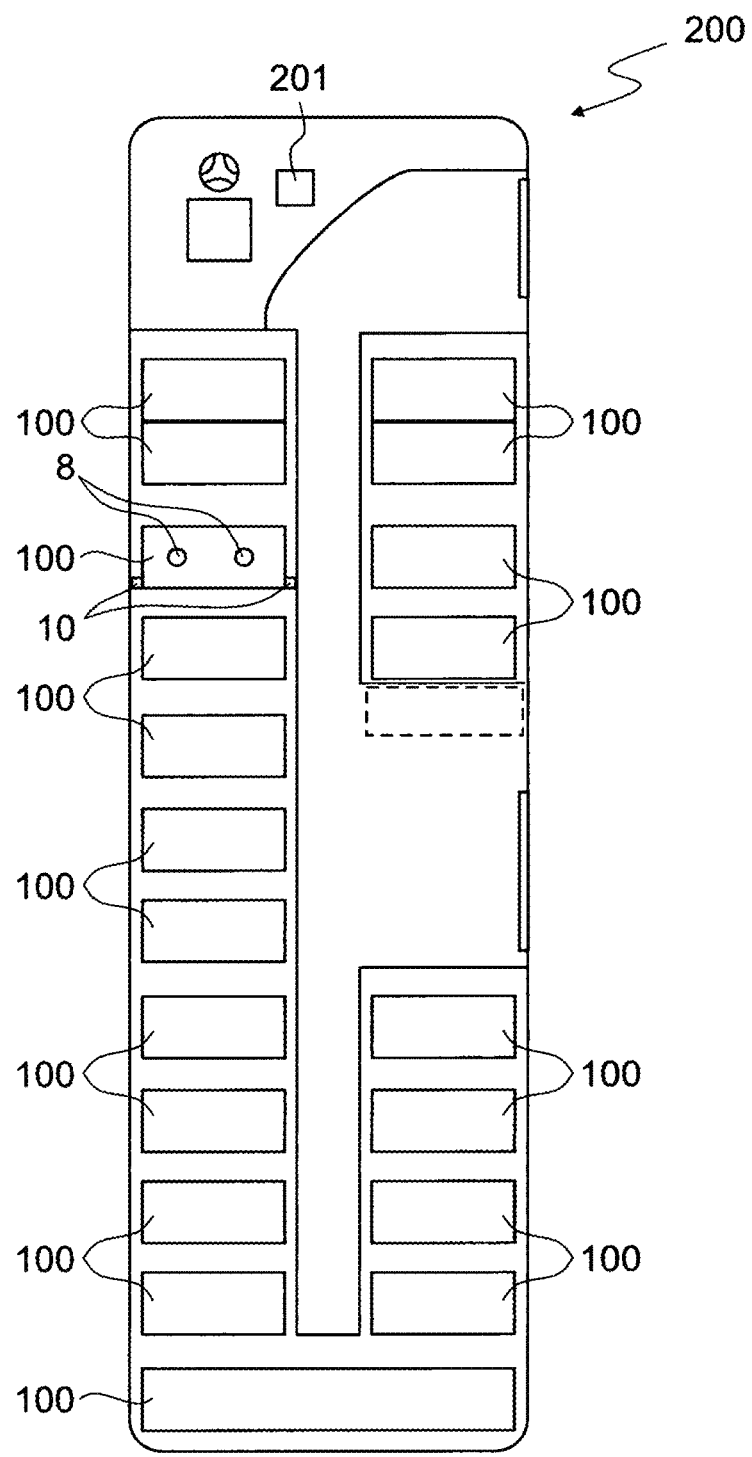
FIG. 8 is a schematic view of a vehicle having several passenger seats and a system for using data.

FIG. 8 shows a vehicle 200, in this case a bus, in which several of the passenger seats 100 are arranged. The passenger seats 100 are each designed in the form of a double seat bench. In principle it would also be possible to design one or more of the passenger seats 100 as single seats.

Furthermore, FIG. 8 shows the main control unit 201 already mentioned above in a very schematic way. The main control unit 201 is operatively connected with the presence sensor 8 and/or the belt sensor 10 of at least one of the passenger seats 100. Data recorded by presence sensor 8 and/or belt sensor 10 as explained above regarding the presence of the passenger or the wearing of the seat belt can be transmitted to the main control unit 201 in this way. Presence sensor 8 or belt sensor 10 can be connected to the main control unit 201 wirelessly or via a corresponding wiring not shown.

The main control unit 201 is part of a system, not shown in its entirety, comprising inter alia the presence sensor 8 and/or the belt sensor 10, for using data obtained from the passenger seat 100 in the commercial vehicle 200 or a rail system in passenger transport, and is designed in such a way that the data recorded by the presence sensor 8 and/or the belt sensor 10 regarding the occupancy of the passenger seat 100 can be compared with stored data regarding the purchase of a ticket by the passenger.

In addition to the connection with the presence sensor 8 and/or belt sensor 10, the main control unit 201 can also be in operative connection with the reading light, the seat heater or heating pad 7, a lumbar support and/or a seat massage element or the massage pad 3, in order to transmit corresponding data on the behavior or general presence of the passenger.

In this way, digital, i.e. computer-aided or programmed processing and profitable exploitation of information on the condition of the passenger and the passenger seat 100 in the vehicle 200 which the passenger has booked online or at another sales location is possible.

The driver can use the main control unit 201 to find out whether all passengers are on board, whether each of the passengers is sitting in the passenger seat 100 he has booked and whether all passengers have fastened their seat belts. Furthermore, the main control unit 201 can be used to centrally switch the lighting, heating and similar systems on and off.

It is also possible to put the main control unit 201 into operation with a monitoring device of an operator of vehicle 200, so that data can be transmitted from the main control unit 201 to the monitoring device of the operator. In the operator's monitoring device, a booking and/or ticketing system in which a booking process for occupying the passenger seat 100 has been completed can also be integrated or connected to the same, so that data recorded by the booking and/or ticketing system can be transmitted to the main control unit 201 and vice versa, i.e. from the main control unit 201 to the booking and/or ticketing system. In this way it is possible to monitor the vehicle presence and to avoid, for example, that a driver of the vehicle 200 sells tickets without the knowledge of the operator of the vehicle 200, but that only passengers who are legalised for this purpose are allowed access to the vehicle 200 or to the passenger seat 100 that they have booked.

Furthermore, statistical evaluations over longer periods of time, for example with regard to the utilisation and loading of the vehicle 200, can be achieved in this way. The periods of use of the above described comfort components of the passenger seat 100 can also be maintained in this way.

Although the present invention has been shown and described herein with respect to certain preferred embodiments and alternative configurations, those were by way of illustration and example only. Accordingly, the spirit and scope of the present invention is intended to be limited only by the terms of the appended claims.

The invention claimed is:

1. A passenger seat used in commercial vehicles and rail systems used in passenger transportation, comprising the following:
    a seat portion on which a passenger sits and which is mounted parallel to a vehicle floor;
    a backrest which is attached to said seat portion and on which the passenger lies back;
    a headrest which is attached to an upper portion of said backrest and on which the passenger rests his/her head;
    an armrest which is attached to at least one side of the passenger seat, is attached to a point of junction of the seat portion and the backrest, and is configured to be opened and closed for allowing the passenger to rest his/her arm;
    a safety belt buckle which is attached to the point of junction of the seat portion and the backrest, to which a safety belt is fastened, the passenger seat further comprising:
        a massage pad which protrudes from the upper portion of the backrest, where the massage pad is covered with fabric, and where the passenger lies back for applying massage; where the massage pad is positioned within the backrest under a top covering, attached to a main frame;
        a compressor generating air which is positioned on a bottom portion of the seat portion facing the floor in order to inflate the massage pad by means of filling with air;
        a plurality of cooling pads which provide air flow from an upper surface of the passenger seat and the seat portion contacting the passenger for cooling the passenger; where a first cooling pad is located between the main frame on the massage pad positioned in the backrest of said passenger seat within the fabric covering the massage pad and a second cooling pad is within the seat portion of the passenger seat;
        a first heating pad which is located between the first cooling pad and the fabric covering the massage pad within the backrest and a second heating pad within the seat portion of said passenger seat in order to heat an upper portion of the seat portion and the backrest contacting the passenger;
        a presence sensor which is positioned between the main frame and the second cooling pad in order to determine whether the passenger is on the passenger seat or not;
        a belt sensor which is integrated into the safety belt buckle which is located at the point of junction of the seat portion and the backrest in order to determine whether the passenger sitting on the passenger seat fastens the safety belt or not;
        a manual control panel positioned on the armrest in order to allow the passenger to control the heating pads, the cooling pads, and the massage pad;
        a wireless connection module which is attached to the passenger seat in order to allow the passenger to control the heating pads, the cooling pads, and the massage pad through a mobile device;
        an identification label which is positioned on the passenger seat for identifying the passenger seat to an application downloaded to the mobile device of the passenger; and
        a control unit where data collected from the presence sensor and the belt sensor are transmitted, is positioned within the vehicle.

2. A passenger seat according to claim 1, further comprising an air pipe which transfers the air generated by the compressor to the massage pad and connects the massage pad and the compressor to each other.

3. A passenger seat according to claim 1, further comprising a charging unit which is positioned on a rear portion of the backrest in order to allow the passenger to charge the mobile device without using a connection cable.

4. A passenger seat according to claim 1, further comprising a holder made of elastic material which is positioned on a rear portion of the backrest in order to keep the mobile device stable during charging.

5. A passenger seat according to claim 1, further comprising a fan which produces air to the cooling pads for cooling the passenger, and is positioned on a bottom surface of the seat portion facing the floor.

6. A passenger seat according to claim 1, further comprising an air channel which connects the cooling pads and a fan to each other in order to transmit the air generated by the fan to the cooling pads.

7. A passenger seat according to claim 1, wherein the heating pads are fabric with electrical resistance.

8. A passenger seat according to claim 1, further comprising a presence sensor transmitter which transmits the information of whether there is the passenger on the passenger seat detected by the presence sensor to the control unit.

9. A passenger seat according to claim 1, further comprising a power unit attached to the passenger seat or vehicle body in order to provide the required energy for the operation of the compressor, the presence sensor, a fan, the belt sensor, a wireless charging unit, a reading lamp and a USB input/output.

10. A passenger seat according to claim 1, wherein the wireless connection module uses wireless technology in order to provide connection between the passenger seat and the mobile device of the passenger.

11. A passenger seat according to claim 1, wherein the application is downloaded on the mobile device of the passenger in order to control/manage the passenger seat.

12. A passenger seat according to claim 1, wherein the identification label is a QR code.

13. A passenger seat according to claim 1, further comprising a control panel where data transmitted to the control unit is displayed.

14. A passenger seat according to claim 1, further comprising a USB input/output positioned on a handle attached to a rear portion of the headrest in order to establish a wired connection for charging the mobile device.

15. A passenger seat according to claim 1, further comprising an energy panel which is attached to a lower portion of the seat portion, in which the compressor, the presence sensor, and the wireless connection module are located.

16. A passenger seat according to claim 1, further comprising a reading lamp which is positioned on a handle located on a rear part of the headrest for the passenger to use in case he/she requires extra light.

* * * * *